(12) United States Patent
Subramaniyam

(10) Patent No.: US 9,228,126 B2
(45) Date of Patent: Jan. 5, 2016

(54) ADDITIVE COMPOSITION FOR CONTROL AND INHIBITION OF POLYMERIZATION OF AROMATIC VINYL MONOMERS, AND METHOD OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 14/363,743

(22) PCT Filed: Dec. 3, 2012

(86) PCT No.: PCT/IN2012/000785
§ 371 (c)(1),
(2) Date: Jun. 6, 2014

(87) PCT Pub. No.: WO2013/108266
PCT Pub. Date: Jul. 25, 2013

(65) Prior Publication Data
US 2014/0350313 A1 Nov. 27, 2014

(30) Foreign Application Priority Data
Dec. 9, 2011 (IN) .......................... 3461/MUM/2011

(51) Int. Cl.
*C07C 7/20* (2006.01)
*C09K 15/20* (2006.01)
*C07B 63/04* (2006.01)
*C09K 15/24* (2006.01)

(52) U.S. Cl.
CPC ................. *C09K 15/20* (2013.01); *C07B 63/04* (2013.01); *C07C 7/20* (2013.01); *C09K 15/24* (2013.01)

(58) Field of Classification Search
CPC ....................................................... C07C 7/20
USPC ........................... 585/2, 3, 4, 5, 952; 203/8, 9
See application file for complete search history.

(56) References Cited

U.S. PATENT DOCUMENTS

| | | | |
|---|---|---|---|
| 3,808,184 A | 4/1974 | Sheth et al. | |
| 4,105,506 A * | 8/1978 | Watson | 585/5 |
| 4,466,905 A * | 8/1984 | Butler et al. | 585/5 |
| 6,403,850 B1 * | 6/2002 | Benage et al. | 585/5 |
| 6,899,806 B2 * | 5/2005 | Benage et al. | 252/403 |
| 7,651,635 B1 * | 1/2010 | Lewis | 252/403 |
| 8,246,858 B2 * | 8/2012 | Nakajima et al. | 252/405 |
| 8,766,027 B1 * | 7/2014 | Subramaniyam | 585/428 |
| 2004/0034247 A1 | 2/2004 | Eldin | |
| 2013/0072729 A1 * | 3/2013 | Link et al. | 585/4 |

FOREIGN PATENT DOCUMENTS

| | | |
|---|---|---|
| EP | 0240297 A1 | 10/1987 |
| IN | 3461MUM2011 | 12/2011 |
| WO | 2013054353 A1 | 4/2013 |
| WO | 2013108266 A1 | 7/2013 |
| WO | 2013108266 A4 | 7/2013 |

OTHER PUBLICATIONS

Foreign communication from the priority application—International Search Report, PCT/IN2012/000785, Oct. 6, 2013, 4 pages.
Foreign communication from the priority application—International Preliminary Report on Patentability, PCT/IN2012/000785, Mar. 21, 2014, 6 pages.

* cited by examiner

*Primary Examiner* — Ellen McAvoy
(74) *Attorney, Agent, or Firm* — Conley Rose, P.C.; Rodney B. Carroll

(57) ABSTRACT

The present invention relates to an improved additive composition for control and inhibition of polymerization of aromatic vinyl monomers including styrene comprising one or more of aromatic nitro compounds and one or more of aliphatic tertiary amines. In one embodiment, the present invention also relates to method of use of presently provided composition. In another embodiment, the present invention also relates to method of controlling and inhibiting polymerization of aromatic vinyl monomers including styrene by employing presently provided composition. In still another embodiment, the present invention also relates to method of preparation of presently provided composition.

24 Claims, No Drawings

ADDITIVE COMPOSITION FOR CONTROL AND INHIBITION OF POLYMERIZATION OF AROMATIC VINYL MONOMERS, AND METHOD OF USE THEREOF

CROSS-REFERENCE TO RELATED APPLICATIONS

This application is a filing under 35 U.S.C. 371 of International Application No. PCT/IN2012/000785 filed Dec. 3, 2012, entitled "Improved Additive Composition for Control and Inhibition of Polymerization of Aromatic Vinyl Monomers, and Method of Use Thereof," which claims priority to Indian Patent Application No. 3461/MUM/2011 filed Dec. 9, 2011, which applications are incorporated by reference herein in their entirety.

FIELD OF THE INVENTION

The present invention relates to an improved additive composition for control and inhibition of polymerization of aromatic vinyl monomers, wherein aromatic vinyl monomer includes styrene, wherein improvement comprises a composition of one or more tertiary amines and one or more of aromatic nitro compounds.

In one embodiment, the present invention relates to use of improved additive composition of present invention to control and inhibit polymerization of aromatic vinyl monomers including styrene, wherein improvement comprises use of a composition comprising one or more tertiary amines and one or more of aromatic nitro compounds.

In another embodiment, the present invention relates to method of preparation of improved additive composition of present invention for control and inhibition of polymerization of aromatic vinyl monomers including styrene, wherein improvement comprises preparation of a composition comprising one or more tertiary amines and one or more of aromatic nitro compounds.

In still another embodiment, the present invention relates to method of controlling and inhibiting polymerization of aromatic vinyl monomers including styrene by employing improved additive composition of present invention, wherein improvement comprises treating the stream containing aromatic vinyl monomers with a composition comprising one or more tertiary amines and one or more of aromatic nitro compounds.

BACKGROUND OF THE INVENTION

The polymerization of aromatic vinyl monomers including styrene during processing is a matter of concern, because it causes formation of unwanted polymers and results in loss of yield of end product and makes the process un-economical.

In the art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders alone is that these are not very effective to reduce polymerization of styrene to a level of substantial inhibition or to the acceptable level of inhibition.

The prior art [U.S. Pat. No. 5,254,760 (US'760)] discloses the polymerization inhibition of vinyl monomers using a combination of nitroxides (i.e. nitroxyl compounds) including 1 oxyl-2,2,6,6,tetramethylpiperidin-4-ol (4HT) and aromatic nitro compounds including dinitro-butylphenol [re abstract, Col. 3, lines 26-32; Col. 4, lines 1-2, 12 of US'760] as the polymerization inhibitor.

The US'760 discloses and teaches use of combination of nitroxides (i.e. nitroxyl) compound and aromatic nitro compound. The US'760 discloses and teaches against the use of either of nitroxides (i.e. nitroxyl) compound or of aromatic nitro compound [Re Col. 5, lines 50-56; Col. 6, lines 10-14 and 42-46; Col. 7, lines 36-41 of US'760].

However, the aromatic nitro compounds including DNBP are to be used in higher amounts and/or are also known for their toxic nature for human exposure [re Col. 1, lines 64-68 of US'760].

Therefore, the industry is aiming for additive composition wherein the amount of aromatic nitro compounds can be reduced or minimized so that the resulted composition is economical as well as safe for human being. Any effort to reduce or minimize consumption of aromatic nitro compounds will lessen the problems of the industry.

NEED OF THE INVENTION

Therefore, there is still a need of an effective additive composition and method of its use and preparation, and method of controlling and inhibiting polymerization of vinyl aromatic monomers by employing said composition, wherein the additive composition is not only suitable for substantial control and inhibition of polymerization of aromatic vinyl monomers including styrene, but also comprises substantially reduced or minimized amount of aromatic nitro compounds.

SUMMARY OF THE INVENTION

Therefore, the present invention aims at providing a solution to above-described existing industrial problems by providing effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises substantially reduced or minimized amount of aromatic nitro compounds.

OBJECTS OF THE INVENTION

Accordingly, the main object of present invention is to provide an effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises substantially reduced or minimized amount of aromatic nitro compounds.

Another main object of present invention is to provide an effective additive composition and method of its use and preparation, and method of controlling and inhibiting polymerization of vinyl aromatic monomers, wherein the additive composition comprises substantially reduced or minimized amount of aromatic nitro compounds, and is still suitable for substantial control and inhibition of polymerization of aromatic vinyl monomers including styrene, and is still required in relatively lower dosage as compared to dosage of aromatic nitro compounds alone for achieving the same or better acceptable level of control and inhibition of polymerization of styrene.

This is also an object of present invention to provide an effective additive composition and method of its use and preparation, and method of controlling and inhibiting polymerization of vinyl aromatic monomers, wherein the additive composition comprises one or more of amines and reduced or minimized amount of one or more of aromatic nitro compounds, and is still suitable for substantial control and inhibition of polymerization of aromatic vinyl monomers including styrene, and is still required in relatively lower dosage as compared to dosage of aromatic nitro compounds alone for achieving the same or better acceptable level of control and inhibition of polymerization of styrene, and wherein the amine is one or more of tertiary amines.

The present invention particularly aims at providing an effective additive composition and method of its use and preparation, and method of controlling and inhibiting polymerization of vinyl aromatic monomers, wherein the additive composition comprises one or more of amines and reduced or minimized amount of one or more of aromatic nitro compounds, and is still suitable for substantial control and inhibition of polymerization of aromatic vinyl monomers including styrene, and is still required in relatively lower dosage as compared to dosage of aromatic nitro compound alone for achieving the same or better acceptable level of control and inhibition of polymerization of styrene, and wherein the amine is one or more of tertiary amines, and therefore, the composition of present invention is not only economical, but is also environment friendly.

The present invention also aims at improving the performance of aromatic nitro compounds at a wider range of temperature including the higher temperature, wherein the composition further comprises one or more tertiary amines.

The present invention also aims at improving the performance of aromatic nitro compounds at a wider range of temperature including the higher temperature and in presence of air, wherein the composition further comprises one or more tertiary amines.

Other objects and advantages of present invention will become more apparent from the following description when read in conjunction with examples, which are not intended to limit scope of present invention.

DETAILED DESCRIPTION OF THE INVENTION

With aim to overcome above-described problems of prior art and to achieve above-described objects of the invention, the inventor has found that when one or more of tertiary amines is added to composition consisting of aromatic nitro compounds, then not only polymerization controlling and inhibiting efficiency of aromatic nitro compounds is substantially improved, but polymerization of aromatic vinyl monomers including styrene, surprisingly and unexpectedly, is also controlled and inhibited to the acceptable level with substantially reduced and minimized dosage of aromatic nitro compound in a composition comprising one or more of tertiary amines and one or more of aromatic nitro compounds, which makes the present composition economical as well as environment friendly.

With aim to overcome above-described problems of prior art and to achieve above-described objects of the invention, the inventor has found that when one or more of an aliphatic tertiary amine, or aliphatic tertiary amine containing one or more hydroxyl groups is added to composition consisting of one or more of aromatic nitro compounds, then not only polymerization controlling and inhibiting efficiency of aromatic nitro compounds is substantially improved, but polymerization of aromatic vinyl monomers including styrene, surprisingly and unexpectedly, is also controlled and inhibited to the acceptable level with substantially reduced and minimized dosage of aromatic nitro compound in a composition comprising one or more aromatic nitro compounds and one or more of aliphatic tertiary amines or aliphatic tertiary amines containing one or more hydroxyl groups, which makes the present composition economical as well as environment friendly.

Accordingly, the present invention relates to additive composition for controlling and inhibition of polymerization of aromatic vinyl monomers including styrene comprising:
(A) one or more of aromatic nitro compounds; and
characterized in that the said composition further comprises:
(B) one or more of aliphatic tertiary amines, or mixture thereof In accordance with present invention, the aliphatic amine is aliphatic tertiary amine, which contains one or more hydroxyl groups, preferably contains one or more hydroxyl groups in the alkyl chain of the tertiary amine, more preferably the aliphatic tertiary amine contains three or four hydroxyl groups in the alkyl chain of the tertiary amine.

In accordance with present invention, in the aliphatic tertiary amine containing one or more hydroxyl groups, the hydroxyl groups are hydroxyalkyl groups.

In accordance with present invention, the hydrocarbon in the aliphatic tertiary amine may be linear, branched or cyclic.

In accordance with present invention, the hydrocarbon in the aliphatic tertiary amine may contain one or more hydroxy alkyl groups.

In accordance with most preferred embodiment of the present invention, the aliphatic tertiary amine containing three hydroxyl groups is tri-isopropanol amine or tris(2-hydroxypropyl)amine [TIPA].

In accordance with one of the preferred embodiments of the present invention, the aliphatic tertiary amine containing hydroxyl groups is N,N,N',N'-Tetrakis(2-hydroxyethyl)ethylene-diamine) (THEED).

In accordance with another preferred embodiment of the present invention, the aliphatic tertiary amine containing hydroxyl groups is N,N,N',N'-Tetrakis(2-hydroxypropyl)ethylene-diamine) (Quadrol®).

In accordance with another preferred embodiment of the present invention, the composition of the present invention may comprise one or more of above-said aliphatic tertiary amines containing hydroxyl groups or mixture thereof.

Therefore, in one embodiment, the present invention relates to additive composition for controlling and inhibition of polymerization of aromatic vinyl monomers including styrene comprising:
(A) one or more of aromatic nitro compounds,
characterized in that the said composition further comprises:
(B) one or more of tertiary amines,
wherein said tertiary amine is selected from a group consisting of:
i) hydroxyl alkyl tertiary amine which is tris(2-hydroxypropyl)amine (TIPA);
ii) propylene oxide treated amine which is N,N,N',N'-Tetrakis(2-hydroxypropyl)ethylene-diamine) (Quadrol®); and
iii) ethylene oxide treated amine is N,N,N',N'-Tetrakis(2-hydroxyethyl)ethylene-diamine) (THEED) THEED compounds; or
iv) mixture thereof.

It has been found that when composition of present invention comprises one or more said aliphatic tertiary amines, the efficiency of aromatic nitro compounds to control and inhibit polymerization of aromatic vinyl monomers including styrene is, surprisingly and unexpectedly, substantially improved to the acceptable level that's too at substantially reduced or minimized dosages of aromatic nitro compounds, thereby making the composition of present invention relatively more economical and environment friendly.

In accordance with one of the embodiments of the present invention, the composition of present invention comprises:
   a) about 40 to about 99.75% by weight of I) one or more of said aromatic nitro compounds; and
   b) about 0.25 to about 60% by weight of II) said amine or mixture thereof.

In accordance with one of the preferred embodiments of the present invention, the composition of present invention is added to the stream containing aromatic vinyl monomers including styrene in an amount varying from about 0.01 ppm to about 2000 ppm, preferably from about 1 ppm to about 2000 ppm by weight of the stream of the monomers including styrene.

In accordance with one of the preferred embodiments of the present invention, the aromatic nitro compound may contain a phenolic group or derivative thereof as well as the nitro group.

In accordance with one of the preferred embodiments of the present invention, the aromatic nitro compound is selected from a group comprising 4,6-dinitro-2-sec-butylphenol (DNBP) and 4,6-dinitro-ortho cresol or 4,6-dinitro-2-hydroxytoluene (DNOC), and mixture thereof.

In accordance with most preferred embodiment of the present invention, the aromatic nitro compound is 4,6-dinitro-2-sec-butylphenol (DNBP).

In accordance with one of the preferred embodiments of the present invention, the present composition does not comprise nitroxide (i.e. nitroxyl) compounds including 1 oxyl-2, 2,6,6, tetramethylpiperidin-4-ol or 4-hydroxy-2,2,6,6-tetramethylpiperidin-1-oxyl (or 4 Hydroxy Tempo or 4-HT).

In accordance with another preferred embodiment of the present invention, the present composition does not comprise:
   i) triethanolamine (TEA);
   ii) Tris[N-butylamine] (TBA);
   iii) monoethanolamine (MEA);
   iv) octyl amine (OA);
   v) dibutyl amine (DBA);
   vi) diethanol amine (DEA);
   vii) dipropyl amine (DPA); and
   viii) ethylene diamine (EDA).

Accordingly, in another embodiment, the present invention also relates to method of using aliphatic tertiary amine and aromatic nitro compounds based additive composition of present invention described herein, a reference to which is drawn in entirety, to control and inhibit polymerization of aromatic vinyl monomers including styrene, wherein the stream comprising aromatic vinyl monomer including styrene is treated with an additive composition comprising one or more of aromatic nitro compounds and one or more of said aliphatic tertiary amines.

In particular, in second embodiment, the present invention relates to a method of using additive composition of the present invention described herein, a reference to which is drawn in entirety, for controlling and inhibition of polymerization of aromatic vinyl monomers including styrene, wherein the stream comprising aromatic vinyl monomer including styrene is treated with the additive composition comprising:
   (A) one or more of aromatic nitro compounds,
      characterized in that the said composition further comprises:
   (B) one or more of tertiary amines,
      wherein said tertiary amine is selected from a group consisting of:
      i) hydroxyl alkyl tertiary amine which is tris(2-hydroxypropyl)amine (TIPA);
      ii) propylene oxide treated amine which is N,N,N',N'-Tetrakis(2-hydroxypropyl)ethylene-diamine) (Quadrol®); and
      iii) ethylene oxide treated amine is N,N,N',N'-Tetrakis(2-hydroxyethyl)ethylene-diamine) (THEED) THEED compounds; or
      iv) mixture thereof.

It may be noted that the stream comprising aromatic vinyl monomers including styrene may be referred to as monomer stream or as aromatic vinyl monomers stream.

In accordance with one of the embodiments of the present invention, the method of using said additive composition of the present invention comprises adding from about 0.01 ppm to about 2000 ppm, preferably from about 1 ppm to about 2000 ppm of said composition to the aromatic vinyl monomers stream including styrene based on weight of the monomers.

In accordance with one of the preferred embodiments of the present invention, one or more of the aromatic nitro compounds and one or more of the aliphatic tertiary amine compounds are added to the monomers stream either individually or after mixing.

It may be noted that all the features of the composition of the present invention described herein, a reference to which is drawn in entirety, are deemed to have been included in present method of using said additive composition of the present invention.

Accordingly, in third embodiment, the present invention also relates to method for controlling and inhibiting polymerization of aromatic vinyl monomers including styrene by employing aliphatic tertiary amine and aromatic nitro compounds based additive composition of present invention described herein, a reference to which is drawn in entirety, wherein the stream comprising aromatic vinyl monomers including styrene is treated with the additive composition comprising one or more of aromatic nitro compounds and one or more of said aliphatic tertiary amines.

In particular, in third embodiment, the present invention relates to a method for controlling and inhibition of polymerization of aromatic vinyl monomers including styrene by adding additive composition of the present invention described herein, a reference to which is drawn in entirety, to the monomers stream, wherein said composition comprises:
   (A) one or more of aromatic nitro compounds,
      characterized in that the said composition further comprises:
   (B) one or more of tertiary amines,
      wherein said tertiary amine is selected from a group consisting of:
      i) hydroxyl alkyl tertiary amine which is tris(2-hydroxypropyl)amine (TIPA);
      ii) propylene oxide treated amine which is N,N,N',N'-Tetrakis(2-hydroxypropyl)ethylene-diamine) (Quadrol®); and
      iii) ethylene oxide treated amine is N,N,N',N'-Tetrakis(2-hydroxyethyl)ethylene-diamine) (THEED) THEED compounds; or
      iv) mixture thereof,
      and said composition is added to said monomers stream.

It may be noted that the stream comprising aromatic vinyl monomers including styrene may be referred to as monomer stream or as aromatic vinyl monomers stream.

In accordance with one of the preferred embodiments of the present invention, the method for controlling and inhibition of polymerization of aromatic vinyl monomers including styrene by employing said additive composition of the present invention comprises adding an amount varying from about 0.01 ppm to about 2000 ppm, preferably from about 1 ppm to about 2000 ppm of the said composition to the aromatic vinyl monomers stream including styrene based on weight of the monomers.

In accordance with one of the preferred embodiments of the present invention, one or more of the aromatic nitro compounds and one or more of the aliphatic tertiary amine compounds are added to the monomers stream either individually or after mixing.

It may be noted that all the features of the composition of the present invention described herein, a reference to which is drawn in entirety, are deemed to have been included in present method for controlling and inhibition of polymerization of aromatic vinyl monomers including styrene by employing said additive composition of the present invention.

In accordance with one of the embodiments of the present invention, the composition of present invention may be mixed with stream containing aromatic vinyl monomers either before the stream enters into processing system or after the stream has entered into processing system, but preferably the composition is added to the stream containing aromatic vinyl monomers before its processing starts so that polymerization of aromatic vinyl monomers is avoided or minimized.

In accordance with one of the embodiments of the present invention, the present composition may be used over a wide range of temperature varying from about 50 degree C. to about 180 degree C., preferably from about 60 degree C. to about 180 degree C.

The composition of present invention may be prepared in any known manner to prepare the compositions.

Accordingly, in fourth embodiment, the present invention also relates to method of preparing aliphatic tertiary amine and aromatic nitro compounds based additive composition of the present invention described herein, a reference to which is drawn in entirety, for controlling and inhibiting polymerization of aromatic vinyl monomers including styrene, wherein one or more of the aromatic nitro compounds are mixed with one or more of the aliphatic tertiary amine compounds either individually or after mixing.

In particular, in fourth embodiment, the present invention relates to a method for preparation of additive composition of the present invention described herein, a reference to which is drawn in entirety, for controlling and inhibition of polymerization of aromatic vinyl monomers including styrene, wherein said method comprises:
  (A) mixing one or more of said aromatic nitro compounds, characterized in that said aromatic nitro compound or mixture thereof is further mixed with one or more of
  (B) said amines selected from a group consisting of:
   i) hydroxyl alkyl tertiary amine which is tris(2-hydroxypropyl)amine (TIPA);
   ii) propylene oxide treated amine which is N,N,N',N'-Tetrakis(2-hydroxypropyl)ethylene-diamine) (Quadrol®); and
   iii) ethylene oxide treated amine is N,N,N',N'-Tetrakis(2-hydroxyethyl)ethylene-diamine) (THEED) THEED compounds; or
   iv) mixture thereof.

In accordance with one of the embodiments of the present invention, the method for preparation of additive composition of the present invention comprises mixing one or more of the tertiary amines with one or more of the aromatic nitro compounds either individually or after mixing.

In accordance with one of the embodiments of the present invention, the composition prepared is used over a range of temperature varying from about 50 degree C. to about 180 degree C., preferably from about 60 degree C. to about 180 degree C.

It may be noted that the stream comprising aromatic vinyl monomers including styrene may be referred to as monomers stream or as aromatic vinyl monomers stream.

It may also be noted that all the features of the composition of the present invention described herein, a reference to which is drawn in entirety, are deemed to have been included in present method for preparation of additive composition of the present invention.

In one of the embodiments, the inventor has found that when present composition comprises any one of the amines selected from a group consisting of N,N,N',N'-Tetrakis(2-hydroxyethyl)ethylene-diamine) (THEED) and N,N,N',N'-Tetrakis(2-hydroxypropyl)ethylene-diamine) (Quadrol®), then efficiency for controlling and inhibition of polymerization of aromatic vinyl monomers including styrene of the aromatic nitro compounds is substantially improved, however, the improvement is not as substantial as for the composition comprising tris(2-hydroxypropyl)amine (TIPA). Therefore, as per most preferred embodiment of the present invention, tris(2-hydroxypropyl)amine (TIPA) is most preferred amine, and as per more preferred embodiment of the present invention, N,N,N',N'-Tetrakis(2-hydroxyethyl)ethylene-diamine) (THEED) and N,N,N',N'-Tetrakis(2-hydroxypropyl)ethylene-diamine) (Quadrol®) are the more preferred amines of the present invention.

It may be noted that, surprisingly and unexpectedly, with increase in concentration of TIPA or Quadrol® or THEED, i.e. when composition comprises about 50% by weight of TIPA or Quadrol® or THEED, the polymerization inhibition efficiency of present additive composition reduces, the reasons for which are not known at present, but compared to prior art additive composition it still demonstrates improvement thereon.

In another embodiment, the inventor has found that when the present composition comprises any one of the amines selected from a group consisting of i) triethanolamine (TEA); ii) Tris[N-butylamine] (TBA); iii) monoethanolamine (MEA); iv) octyl amine (OA); v) dibutyl amine (DBA); vi) diethanol amine (DEA); vii) dipropyl amine (DPA); and viii) ethylene diamine (EDA), then efficiency for controlling and inhibition of polymerization of aromatic vinyl monomers including styrene of the aromatic nitro compounds is, surprisingly and unexpectedly, substantially reduced. Therefore, in one embodiment, the present composition does not comprise any one of the amines selected from a group consisting of i) triethanolamine (TEA); ii) Tris[N-butylamine] (TBA); iii) monoethanolamine (MEA); iv) octyl amine (OA); v) dibutyl amine (DBA); vi) diethanol amine (DEA); vii) dipropyl amine (DPA); and viii) ethylene diamine (EDA). It may be noted that some of these amines result in very marginal improvement in efficiency of aromatic nitro compounds at lower amounts, but same is not commercially viable.

Further advantages and embodiments of the present invention will become more apparent from the following examples.

The present invention is now described with the help of following examples, which are not intended to limit scope of the present invention, but have been incorporated to illustrate mode and best mode of performing the present invention.

EXPERIMENTS

Main Experiment

In the following experiments, measured amount of distilled styrene (or hydrocarbon stream in gms) and measured amount of additives (in ppm by weight of styrene or hydrocarbon stream) were taken in a tube reactor equipped with thermometer and nitrogen inlet and outlet. In these experiments a tube reactor was used without any mechanical stirrer, and enough $N_2$ flow was maintained to ensure proper agitation. The reactions were carried out at either 120° C. (Table-I, Table III, Table IV, Table V and Table VI) or 135° C. (Table-II) for 2 hours. After the selected duration, the reactor was cooled to below 10° C. by immersing in crushed ice. The contents of the reactor were then poured in a beaker. To this same beaker, approximately for 1.5-2 g chilled polymerization mixture, about 80 g methanol was used to precipitate the polymer formed in the styrene solution. The precipitate obtained was filtered, dried to remove methanol, and weighed. The weight of the precipitate was reported as % polymer formed.

It may be noted that styrene was purified before use to remove the stabilizers.

In the following examples, the prior additive is aromatic nitro compound, which is 4,6-dinitro-2-sec-butylphenol (DNBP), which was taken in an amount of about 100, 200, 300, 400, 500, 600 or 1000 ppm by weight of styrene (or hydrocarbon stream).

In the following examples, the present additive is a composition comprising about 100, 200, 300, 500 or 1000 ppm of aromatic nitro compound, which is 4,0-dinitro-2-sec-butylphenol (DNBP), and from about 1 to 20 ppm of aliphatic tertiary amine, which is tri-isopropanol amine (TIPA) containing three hydroxyl groups, wherein from about 1 to about 20 ppm of TIPA is added to the weighed amount of aromatic nitro compound.

Experiment 1

The results of above Main Experiment when performed with 10 g of distilled styrene by heating to 120° C. for 2 h are provided in Table-I.

TABLE I

| Active Dosage of Prior art Additive (ppm) ↓ | % polymer formed with Prior art Additive | Active Dosage of Present composition (ppm) ↓ | % polymer formed with Present composition | Technical Effects of present composition |
|---|---|---|---|---|
| 100 ppm | 4.8 | 100 + 1 TIPA | 1.82 | Polymerization |
|  |  | 100 + 2 TIPA | 1.45 | inhibition efficiency of |
|  |  | 100 + 3 TIPA | 1.22 | aromatic nitro |
|  |  | 100 + 4 TIPA | 1.08 | compound is |
| 200 ppm | 3.18 | 100 + 1 TIPA | 1.82 | substantially improved, |
|  |  | 100 + 2 TIPA | 1.45 | and % polymer formed is |
|  |  | 100 + 3 TIPA | 1.22 | substantially reduced on |
|  |  | 100 + 4 TIPA | 1.08 | addition of aliphatic |
| 300 ppm | 2.03 | 100 + 1 TIPA | 1.82 | tertiary amine in |
|  |  | 100 + 2 TIPA | 1.45 | aromatic nitro |
|  |  | 100 + 3 TIPA | 1.22 | compound. |
|  |  | 100 + 4 TIPA | 1.08 |  |

It is understood from above Table-I that when just 1 ppm, 2 ppm, 3 ppm or 4 ppm of TIPA is added to 100 ppm of DNBP (prior art additive), the efficiency of DNBP to control and inhibit polymerization of styrene is, surprisingly and unexpectedly, improved substantially.

It can also be seen from Table-I that polymerization of styrene is, surprisingly and unexpectedly, substantially reduced just on addition of 1 ppm, 2 ppm, 3 ppm or 4 ppm of TIPA in 100 ppm of DNBP (prior art additive).

It may be noted, the % polymer formed is, surprising and unexpectedly, reduced from 4.8% with 100 ppm of DNBP, or from 3.18% with 200 ppm of DNBP, or from 2.03% with 300 ppm of DNBP to 1.82% when present composition comprises 100 ppm of DNBP and 1 ppm of TIPA, to 1.45% when present composition comprises 100 ppm of DNBP and 2 ppm of TIPA, to 1.22% when present composition comprises 100 ppm of DNBP and 3 ppm of TIPA, to 1.08% when present composition comprises 100 ppm of DNBP and 4 ppm of TIPA meaning thereby, the present composition results in substantial saving of dosage of DNBP (aromatic nitro compound), and hence, is more economical and environment friendly than a composition consisting of aromatic nitro compound.

Experiment 2

The results of above Main Experiment when performed with 10 g of distilled styrene by heating to 135° C. for 2 h are provided in Table-II.

TABLE II

| Active Dosage of Prior art Additive (ppm) ↓ | % polymer formed with Prior art Additive | Active Dosage of Present composition (ppm) ↓ | % polymer formed with Present composition | Technical Effects of present composition |
|---|---|---|---|---|
| 500 ppm | 4.13 | 500 + 5 TIPA | 2.24 | Polymerization inhibition |
|  |  | 500 + 10 TIPA | 2.03 | efficiency of aromatic |
|  |  | 500 + 15 TIPA | 1.88 | nitro compound is |
|  |  | 500 + 20 TIPA | 1.79 | substantially improved, |

TABLE II-continued

| Active Dosage of Prior art Additive (ppm) ↓ | % polymer formed with Prior art Additive | Active Dosage of Present composition (ppm) ↓ | % polymer formed with Present composition | Technical Effects of present composition |
|---|---|---|---|---|
| 1000 ppm | 1.79 | 500 + 20 TIPA | 1.79 | and % polymer formed is substantially reduced on addition of aliphatic tertiary amine in aromatic nitro compound. |

It is understood from above Table-II that when just 5 to 20 ppm of TIPA is added even to higher dosage of 500 ppm of DNBP (prior art additive), and styrene stream with additive is treated even at higher temperature of 135° C., the efficiency of DNBP to control and inhibit polymerization of styrene is, surprisingly and unexpectedly, improved substantially.

It can also be seen from Table-II that polymerization of styrene is, surprisingly and unexpectedly, substantially reduced just on addition of 5 to 20 ppm of TIPA in 500 ppm of DNBP (prior art additive).

It may be noted, the % polymer formed is, surprising and unexpectedly, reduced from 4.13% with 500 ppm of DNBP to 2.24% when present composition comprises 500 ppm of DNBP and 5 ppm of TIPA, to 2.03% when present composition comprises 500 ppm of DNBP and 10 ppm of TIPA, to 1.88% when present composition comprises 500 ppm of DNBP and 15 ppm of TIPA, to 1.79% when present composition comprises 500 ppm of DNBP and 20 ppm of TIPA, and on the contrary, the efficiency of 1.79% polymer formed could only be achieved when 1000 ppm of DNBP (aromatic nitro compound—prior art additive) is used, meaning thereby, the present composition results in substantial saving of up to about half of the dosage of DNBP (aromatic nitro compound—prior art additive), and hence, is more economical and environment friendly than a composition consisting of aromatic nitro compound.

Experiments 3 to 5

In the following examples, for above Main Experiment, the prior art additive composition is DNBP being aromatic nitro compound, which is taken in an amount of about 100, 200, 300, 400, 500 and 600 ppm, and the present additive composition is a composition comprising DNBP being aromatic nitro compound, and additionally comprising TIPA, THEED or Quadrol® being amines of the present invention, which are taken in weight ratio of DNBP:Amine ratio of 99:1, 95:5, 90:10, 85:15, and 50:50, the composition is made to 100, 200 and 300 ppm. The inventor has further compared the results of present compositions with additive compositions comprising DNBP and amine selected from a group consisting of TEA, TBA, MEA, OA DBA, DEA DPA, and EDA for comparative purposes. The results are given in Tables III, IV, V and VI.

TABLE III

| Additive | Active dosage, ppm | % Polymer formed |
|---|---|---|
| DNBP | 100 | 4.8 |
|  | 200 | 3.18 |
|  | 300 | 2.03 |
|  | 400 | 1.17 |
|  | 500 | 0.92 |
|  | 600 | 0.60 |

As can be seen from data in Tables IV, V and VI, with addition of about 1 to about 150 ppm of TIPA, THEED or Quadrol® to DNBP making total of 100, 200 and 300 ppm of the composition so as to have DNBP:Amine in a weight ratio of 99:1, 95:5, 90:10, 85:15, and 50:50, the efficiency of prior art additive composition consisting of DNBP to control and inhibit polymerization of styrene is, surprisingly and unexpectedly, substantially improved.

As can be seen, when present composition comprises any one of the amines selected from a group consisting of N,N,N',N'-Tetrakis(2-hydroxyethyl)ethylene-diamine) (THEED) and N,N,N',N'-Tetrakis(2-hydroxypropyl)ethylene-diamine) (Quadrol®), then efficiency for controlling and inhibition of polymerization of aromatic vinyl monomers including styrene of the aromatic nitro compound is substantially improved, however, the improvement is not as substantial as for the composition comprising tris(2-hydroxypropyl)amine (TIPA). Therefore, as per most preferred embodiment of the present invention, tris(2-hydroxypropyl)amine (TIPA) is most preferred amine, and N,N,N',N'-Tetrakis(2-hydroxyethyl)ethylene-diamine) (THEED) and N,N,N',N'-Tetrakis(2-hydroxypropyl)ethylene-diamine) (Quadrol®) are the more preferred amines of the present invention.

As can also be seen, when the composition comprises any one of the comparative amines selected from a group consisting of TEA, TBA, MEA, OA DBA, DEA DPA, and EDA, then efficiency for controlling and inhibition of polymerization of aromatic vinyl monomers including styrene of the aromatic nitro compounds is not improved. Therefore, in one of the embodiments, the present composition does not comprise any one of the amines selected from a group consisting of TEA, TBA, MEA, OA DBA, DEA DPA, and EDA. It may be noted that some of these amines result in very marginal improvement in efficiency of aromatic nitro compounds, but same is not commercially viable.

It may be noted that, surprisingly and unexpectedly, with increase in concentration of amine, i.e. when about 50% of the amine is added to DNBP, the polymerization inhibition efficiency of present additive composition reduces marginally, the reasons for which are not known at present.

Accordingly, in view of above experimental data and analysis thereof, it can be concluded that only the additive compositions of the present invention comprising aromatic nitro compound and amine selected from a group consisting of TIPA, THEED and Quadrol®, surprisingly and unexpectedly, result in improvement of control and polymerization inhibition efficiency of prior art additive composition consisting of aromatic nitro compound, and these findings confirm synergistic effect of present compositions.

All of above findings confirm synergistic, surprising and unexpected effects of present composition at lower as well as at higher temperatures.

All of above findings also confirm that there is successive increase in efficiency of prior art additive to control and inhibit polymerization of aromatic vinyl monomers, preferably of styrene.

All of above findings also confirm that present composition is capable of achieving far better efficiency to control and inhibit polymerization of aromatic vinyl monomers, preferably of styrene with same dosage of the prior art additive, meaning thereby, the present invention results in economical and environmental benefits.

Above experimental results also confirm that presently provided composition is far superior than prior art additive, and hence, has technical advantages and surprising effects over the prior art additive.

It may be noted that the term "about" as employed herein is not intended to enlarge scope of claimed invention, but has been incorporated only to include experimental errors permissible in the field of the art.

TABLE IV

| Active Dosage Ratio of DNBP: Amine | Total Dosage (ppm) | Active Dosage DNBP + Amine | DNBP | DNBP + TIPA | DNBP + THEED | DNBP + Quadrol ® | DNBP + TBA | DNBP + MEA |
|---|---|---|---|---|---|---|---|---|
| 99:1 | 100 | 99 + 1 | 4.8 | 1.83 | 2.84 | 2.95 | 3.84 | 4.53 |
| 95:5 | 100 | 95 + 5 | 4.8 | 1.05 | 2.32 | 2.45 | 4.95 | 4.87 |
| 90:10 | 100 | 90 + 10 | 4.8 | 0.83 | 1.75 | 1.95 | 5.20 | 5.10 |
| 85:15 | 100 | 85 + 15 | 4.8 | 0.72 | 1.43 | 1.50 | 5.82 | 5.52 |
| 50:50 | 100 | 50 + 50 | 4.8 | 1.90 | 2.50 | 2.70 | 6.9 | 6.9 |

| Active Dosage Ratio of DNBP: Amine | DNBP + DBA | DNBP + TEA | DNBP + Octyl amine | DNBP + DEA | DNBP + DPA | DNBP + EDA |
|---|---|---|---|---|---|---|
| 99:1 | 4.67 | 4.78 | 4.74 | 4.47 | 4.58 | 4.8 |
| 95:5 | 4.95 | 4.91 | 4.85 | 5.05 | 5.03 | 4.96 |
| 90:10 | 5.15 | 5.03 | 5.17 | 5.30 | 5.25 | 5.15 |
| 85:15 | 5.61 | 5.21 | 5.72 | 5.65 | 5.50 | 5.35 |
| 50:50 | 7.0 | 7.15 | 6.9 | 7.6 | 7.05 | 7.35 |

TABLE V

| Active Dosage Ratio of DNBP: Amine | Total Dosage (ppm) | Active Dosage DNBP + Amine | DNBP | DNBP + TIPA | DNBP + THEED | DNBP + Quadrol ® | DNBP + TBA | DNBP + TEA |
|---|---|---|---|---|---|---|---|---|
| 99:1 | 200 | 198 + 2 | 3.18 | 0.93 | 1.82 | 1.96 | 3.02 | 3.13 |
| 95:5 | 200 | 190 + 10 | 3.18 | 0.65 | 1.40 | 1.52 | 3.25 | 3.33 |
| 90:10 | 200 | 180 + 20 | 3.18 | 0.56 | 0.9 | 1.10 | 3.43 | 3.50 |
| 85:15 | 200 | 170 + 30 | 3.18 | 0.35 | 0.75 | 0.9 | 3.85 | 3.75 |
| 50:50 | 200 | 100 + 100 | 3.18 | 0.86 | 1.60 | 1.90 | 4.6 | 5.05 |

| Active Dosage Ratio of DNBP: Amine | DNBP + MEA | DNBP + DPA | DNBP + DBA | DNBP + DEA | DNBP + Octyl amine | DNBP + EDA |
|---|---|---|---|---|---|---|
| 99:1 | 3.12 | 3.21 | 3.25 | 3.31 | 3.33 | 3.25 |
| 95:5 | 3.35 | 3.40 | 3.45 | 3.60 | 3.51 | 3.40 |
| 90:10 | 3.52 | 3.62 | 3.80 | 3.91 | 3.91 | 3.6 |
| 85:15 | 3.8 | 3.85 | 4.1 | 4.1 | 4.5 | 3.8 |
| 50:50 | 5.2 | 4.9 | 5.1 | 5.5 | 5.1 | 5.65 |

TABLE VI

| Active Dosage Ratio of DNBP: Amine | Total Dosage (ppm) | Active Dosage DNBP + Amine | DNBP | DNBP + TIPA | DNBP + THEED | DNBP + Quadrol ® | DNBP + MEA | DNBP + DPA |
|---|---|---|---|---|---|---|---|---|
| 99:1 | 300 | 297 + 3 | 2.03 | 0.35 | 0.70 | 0.75 | 1.85 | 1.95 |
| 95:5 | 300 | 285 + 15 | 2.03 | 0.20 | 0.45 | 0.50 | 2.05 | 2.15 |
| 90:10 | 300 | 270 + 30 | 2.03 | 0.07 | 0.21 | 0.35 | 2.45 | 2.52 |

TABLE VI-continued

| | | | | | | | | |
|---|---|---|---|---|---|---|---|---|
| 85:15 | 300 | 255 + 45 | 2.03 | 0.05 | 0.15 | 0.30 | 3.0 | 2.9 |
| 50:50 | 300 | 150 + 150 | 2.03 | 0.35 | 0.90 | 0.80 | 4.1 | 3.8 |

| Active Dosage Ratio of DNBP: Amine | DNBP + TEA | DNBP + Octyl amine | DNBP + DBA | DNBP + TBA | DNBP + DEA | DNBP + EDA |
|---|---|---|---|---|---|---|
| 99:1 | 2.01 | 1.98 | 2.05 | 2.15 | 2.10 | 2.06 |
| 95:5 | 2.10 | 2.10 | 2.20 | 2.30 | 2.35 | 2.19 |
| 90:10 | 2.42 | 2.7 | 2.62 | 2.81 | 2.75 | 2.30 |
| 85:15 | 2.8 | 3.2 | 2.92 | 3.09 | 3.25 | 2.45 |
| 50:50 | 3.9 | 4.0 | 3.90 | 3.5 | 4.2 | 4.3 |

The invention claimed is:

1. Additive composition for controlling and inhibition of polymerization of aromatic vinyl monomers including styrene consisting of:
   (A) one or more of aromatic nitro compounds,
   characterized in that the said composition further consists of:
   (B) one or more of aliphatic tertiary amines, or mixture thereof,
   wherein the aliphatic tertiary amine contains one or more hydroxyl groups in the alkyl chain of the tertiary amine.

2. The additive composition as claimed in claim 1, wherein the aliphatic tertiary amine contains three or four hydroxyl groups in the alkyl chain of the tertiary amine.

3. The additive composition as claimed in claim 1, wherein said hydroxyl groups of the aliphatic tertiary amine are hydroxyalkyl groups.

4. The additive composition as claimed in claim 1, wherein said aliphatic tertiary amine contains three hydroxyl groups and is tri-isopropanol amine or tris(2-hydroxypropyl)amine (TIPA).

5. The additive composition as claimed in claim 1, wherein said aliphatic tertiary amine contains hydroxyl groups and is N,N,N',N'-Tetrakis (2-hydroxyethyl) ethylene-diamine (THEED).

6. The additive, composition as claimed in claim 1, wherein said aliphatic tertiary amine contains hydroxyl groups and is N,N,N',N'-Tetrakis (2-hydroxypropyl) ethylene-diamine.

7. Additive composition for controlling and inhibition of polymerization of aromatic vinyl monomers including styrene, wherein the composition comprises:
   (A) one or more of aromatic nitro compounds,
   characterized in that the said composition further comprises:
   (B) one or more of aliphatic tertiary amines, or mixture thereof,
   wherein the aliphatic tertiary amine contains on or more hydroxyl groups in the alkyl chain of the tertiary amine,
   wherein said tertiary amine is selected from a group consisting of:
   i) hydroxyl alkyl tertiary amine;
   ii) propylene oxide treated amine; and
   iii) ethylene oxide treated amine; or
   iv) mixture thereof,
   wherein
   said hydroxyl alkyl tertiary amine is tris(2-hydroxypropyl) amine (TIPA):
   said propylene oxide treated amine is N,N,N',N'-Tetrakis (2-hydroxypropyl) ethylene-diamine (Quadrol®); and
   said ethylene oxide treated amine is N,N,N',N'-Tetrakis (2-hydroxypropyl) ethylene-diamine (THEED).

8. The additive composition as claimed in claim 1, wherein said composition consists of:
   a) about 40 to about 99.75% by weight of I) one or more of said aromatic nitro compounds; and
   b) about 0.25 to about 60% by weight of II) said amine or mixture thereof.

9. The additive composition as claimed in claim 1, wherein about 0.01 to about 2000 ppm of said composition is added to aromatic vinyl monomers stream based on weight of monomer.

10. The additive composition as claimed in claim 1, wherein said aromatic nitro compound contains a phenolic group or derivative thereof as well as the nitro group.

11. The additive composition as claimed in claim 1, wherein said aromatic nitro compound is selected from a group comprising 4,6-dinitro-2-sec-butylphenol (DNBP) and 4,6-dinitro-ortho cresol or 4,6-dinitro-2-hydroxytoluene (DNOC), and mixture thereof.

12. The additive composition as claimed in claim 1, wherein said aromatic nitro compound is 4,6-dinitro-2-sec-butylphenol (DNBP).

13. The additive composition as claimed in claim 1, wherein said composition does not comprise nitroxide (i.e. nitroxyl) compounds including 1 oxyl-2,2,6,6,tetramethylpiperidin-4-ol or 4-hydroxy-2,2,6,6-tetramethylpiperidin-1-oxyl (or 4Hydroxy Tempo or 4-HT).

14. The additive composition as claimed in claim 1, wherein said composition does not comprise:
   i) triethanolamine (TEA);
   ii) Tris [N-butylamine] (TBA);
   iii) monoethanolamine (MEA);
   iv) octyl amine (OA);
   v) dibutyl amine (DBA);
   vi) diethanol amine (DEA);
   vii) dipropyl amine (DPA); and
   viii) ethylene diamine (EDA).

15. A method for controlling and inhibition of polymerization of aromatic vinyl monomers including styrene by adding additive composition as claimed in claim 1 to monomers stream, wherein said composition consists of:
   (A) one or more of aromatic nitro compounds,
   characterized in that the said composition further consists of:
   (B) one or more of the aliphatic tertiary amines, or mixture thereof,
   wherein the aliphatic tertiary amine contains one or more hydroxyl groups in the alkyl chain of the tertiary amine, and said composition is added to said monomers stream.

16. The method as claimed in claim 15, wherein about 0.01 to about 2000 ppm of said composition is added to aromatic vinyl monomers stream based on weight of monomer.

17. The method as claimed in claim 15, wherein one or more of said aromatic nitro compounds and one or more of said tertiary amine compounds are added to said monomers stream either individually or after mixing.

18. A method of using additive composition as claimed in claim 1 for controlling and inhibition of polymerization of aromatic vinyl monomers including styrene, wherein the stream comprising aromatic vinyl monomer including styrene is treated with the additive composition consisting of:

(A) one or more of aromatic nitro compounds, characterized in that the said composition further consists of:

(B) one or more of the aliphatic tertiary amines, or mixture thereof, wherein the aliphatic tertiary amine contains one or more hydroxyl groups in the alkyl chain of the tertiary amine.

19. The method as claimed in claim 18, wherein said aromatic vinyl monomers stream is treated with about 0,01 to about 2000 ppm of said composition based on weight of monomer.

20. The method as claimed in claim 18, wherein one or more of said aromatic nitro compounds and one or more of said tertiary amine compounds are added to said monomers stream either individually or after mixing.

21. A method for preparing additive composition as claimed in claim 1 for controlling and inhibiting polymerization of aromatic vinyl monomers including styrene, wherein the method comprises:

(A) mixing one or more of said aromatic nitro compounds, characterized in that said aromatic nitro compound or mixture thereof is further mixed with one or more of (B) said aliphatic tertiary amines, or mixture thereof, wherein the aliphatic tertiary amine contains one or more hydroxyl groups in the alkyl chain of the tertiary amine.

22. The method as claimed in claim 21, wherein one or more of said amines are mixed with one or more of said aromatic nitro compounds either individually or after mixing.

23. The method as claimed in claim 15, wherein said composition is used over a range of temperature varying from about 50 degree C. to about 180 degree C.

24. The method as claimed in claim 18, wherein said composition is used over a range of temperature varying from about 50 degree C. to about 180 degree C.

* * * * *

UNITED STATES PATENT AND TRADEMARK OFFICE
CERTIFICATE OF CORRECTION

PATENT NO.        : 9,228,126 B2
APPLICATION NO.   : 14/363743
DATED             : January 5, 2016
INVENTOR(S)       : Mahesh Subramaniyam It is certified that error appears in the above-identified patent and that said Letters Patent is hereby corrected as shown below:

In the Claims:

Claim 1, col. 15, line 50, replace "contains on or more" with --contains one or more--.

Claim 7, col. 15, line 63, replace "(2-hydroxypropyl)" with --(2-hydroxyethyl)--.

Claim 19, col. 17, line 12, replace "about 0,01 to" with --about 0.01 to--.

Signed and Sealed this
Nineteenth Day of April, 2016

Michelle K. Lee
*Director of the United States Patent and Trademark Office*